US008741269B2

(12) United States Patent
Mandadi et al.

(10) Patent No.: US 8,741,269 B2
(45) Date of Patent: Jun. 3, 2014

(54) NON-AQUEOUS DENTIFRICE COMPOSITION WITH BIOACCEPTABLE AND BIOACTIVE GLASS AND METHODS OF USE AND MANUFACTURE THEREOF

(75) Inventors: Prakasarao Mandadi, Flemington, NJ (US); Suman K. Chopra, Monroe, NJ (US); Lynette Zaidel, Cranford, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/260,786

(22) PCT Filed: Apr. 1, 2010

(86) PCT No.: PCT/US2010/029682
§ 371 (c)(1),
(2), (4) Date: Sep. 28, 2011

(87) PCT Pub. No.: WO2010/115037
PCT Pub. Date: Oct. 7, 2010

(65) Prior Publication Data
US 2012/0020898 A1    Jan. 26, 2012

Related U.S. Application Data

(60) Provisional application No. 61/165,795, filed on Apr. 1, 2009.

(51) Int. Cl.
| A61Q 11/00 | (2006.01) |
| A61K 8/02 | (2006.01) |
| A61K 8/18 | (2006.01) |
| A61K 8/21 | (2006.01) |
| A61K 8/25 | (2006.01) |
| A61K 8/29 | (2006.01) |
| A61K 8/73 | (2006.01) |
| A61K 6/00 | (2006.01) |

(52) U.S. Cl.
USPC .............. 424/49; 424/401; 424/488; 424/52; 424/57; 433/215; 433/216; 433/217.1

(58) Field of Classification Search
USPC ........ 424/49, 52, 57, 401, 488; 433/215, 216, 433/217.1
See application file for complete search history.

(56) References Cited

U.S. PATENT DOCUMENTS

| 3,574,824 A | 4/1971 | Kapadia |
| 3,863,006 A | 1/1975 | Hodosh |
| 5,160,737 A | 11/1992 | Friedman et al. |
| 5,330,746 A | 7/1994 | Friedman et al. |
| 5,670,137 A | 9/1997 | Ascione |
| 5,735,942 A | 4/1998 | Litkowski et al. |
| 5,834,008 A | 11/1998 | Greenspan et al. |
| 5,843,409 A | 12/1998 | Campbell et al. |
| 5,851,513 A | 12/1998 | Brahms et al. |
| 5,891,233 A | 4/1999 | Salonen et al. |
| 5,972,384 A | 10/1999 | Thut et al. |
| 5,977,204 A | 11/1999 | Boyan et al. |
| 5,990,380 A | 11/1999 | Marotta et al. |
| 6,086,374 A | 7/2000 | Litkowski et al. |
| 6,096,292 A | 8/2000 | Halecky et al. |
| 6,190,643 B1 | 2/2001 | Stoor et al. |
| 6,244,871 B1 | 6/2001 | Litkowski et al. |
| 6,306,925 B1 | 10/2001 | Clupper et al. |
| 6,338,751 B1 | 1/2002 | Litkowski et al. |
| 6,342,207 B1 | 1/2002 | Stoor et al. |
| 6,344,496 B1 | 2/2002 | Niederauer et al. |
| 6,365,132 B1 | 4/2002 | Litkowski et al. |
| 6,423,343 B1 | 7/2002 | Lee et al. |
| 6,663,878 B1 | 12/2003 | Greenspan et al. |
| 6,689,341 B2 | 2/2004 | Galli |
| 6,756,060 B1 | 6/2004 | Greenspan et al. |
| 2004/0086467 A1 | 5/2004 | Curro |
| 2005/0142077 A1* | 6/2005 | Zimmer et al. ................. 424/57 |
| 2006/0008424 A1 | 1/2006 | MacDonald et al. |
| 2007/0231277 A1 | 10/2007 | Sharma et al. |
| 2007/0258916 A1 | 11/2007 | Ferracane et al. |
| 2007/0264291 A1 | 11/2007 | Greenspan et al. |
| 2008/0171000 A1* | 7/2008 | Engelman et al. ............. 424/50 |
| 2009/0092562 A1 | 4/2009 | Zaidel et al. |
| 2009/0208428 A1 | 8/2009 | Hill et al. |
| 2009/0269287 A1* | 10/2009 | Berta .............................. 424/52 |
| 2009/0324516 A1 | 12/2009 | Muscle et al. |

FOREIGN PATENT DOCUMENTS

| CN | 101407373 | 4/2009 |
| DE | 102004050954 | 4/2006 |
| EP | 0381445 | 8/1990 |

(Continued)

OTHER PUBLICATIONS

Azouka et al., 1993, "The production of shellac and its general and dental uses: a review," J. Oral Rehabilitation 20:393-400.
Blixt et al., 1993, "The influence of lining techniques on the marginal seal of Class II composite resin restorations," Quintessence International 24(3):203-210.
Gorustovich et al., 2007, "Osteoconductivity of Strontium-Doped Bioactive Glass Particles," Bone 41(6):S4 Abstract.
Klineberg et al., 1967, "Physical properties of shellac baseplate materials," Australian Dental J. 12(5):468-475.
Kokubo, 1990, "Surface Chemistry of Bioactive Glass-Ceramics," J. of Non-Crystalline Solids 120:138-151.

(Continued)

Primary Examiner — Lezah Roberts
(74) Attorney, Agent, or Firm — Howard C. Lee

(57) ABSTRACT

The invention encompasses non-aqueous dentifrice compositions containing a bioacceptable and bioactive glass with improved mouth-feel, foam, and product stability. More particularly, the invention encompasses non-aqueous compositions including combinations including carrageenan and/or carboxymethylcellulose gums, glycerin, ethylene oxide/propylene oxide copolymers, and a bioactive glass and methods of use the compositions in an oral care product, for example, a whitening tooth-paste, for hypersensitive teeth.

25 Claims, 3 Drawing Sheets

(56) References Cited

FOREIGN PATENT DOCUMENTS

| | | |
|---|---|---|
| EP | 0975284 | 2/2000 |
| EP | 1018978 | 7/2000 |
| EP | 1049457 | 11/2000 |
| EP | 1123072 | 8/2001 |
| EP | 0833602 | 9/2001 |
| EP | 1185247 | 3/2002 |
| EP | 1272144 | 1/2003 |
| EP | 0804136 | 5/2003 |
| EP | 1333796 | 8/2003 |
| EP | 0877716 | 10/2004 |
| EP | 1011621 | 6/2005 |
| EP | 1339381 | 10/2005 |
| EP | 0868903 | 11/2006 |
| EP | 1729722 | 12/2006 |
| EP | 1021148 | 5/2008 |
| EP | 1143919 | 10/2008 |
| JP | 10167942 | 6/1998 |
| WO | WO 96/10985 | 4/1996 |
| WO | WO 99/13852 | 3/1999 |
| WO | WO 01/72262 | 10/2001 |
| WO | WO 02/38119 | 5/2002 |
| WO | WO 2005/063185 | 7/2005 |
| WO | WO 2006/055317 | 5/2006 |
| WO | WO 2007/063508 | 6/2007 |
| WO | WO 2007/064885 | 6/2007 |
| WO | WO 2007/144662 | 12/2007 |
| WO | WO 2009/158564 | 12/2009 |
| WO | WO 2011/050369 | 4/2011 |

OTHER PUBLICATIONS

Lee et al., 1991, "The effect of bead attachment systems on casting patterns and resultant tensile bond strength of composite resin veneer cast restorations," J. Prosthetic Dentistry 66(5):623-630.

Marini et al., "Pilot Clinical Study Evaluating Efficacy of NovaMin-Containing Dentifrice for Relief of Dentin Hypersensitivity," NovaMin Research Report, May 2006.

Pashley et al., "Dentin permeability. Effects of desensitizing dentifrices in vitro," 1984, J. Periodontol. 55(9):522-525.

Zhang et al.,1998, "The effects of Pain-Free Desensitizer on dentine permeability and tubule occlusion over time, in vitro," J. Clin. Periodontol. 25(11 Pt. 1):884-891.

ISR & Written Opinion for PCT/US2010/029682 mailed on Apr. 3, 2012.

ISR & Written Opinion for PCT/US2010/029684 mailed on Apr. 4, 2012.

ISR & Written Opinion for PCT/US2010/029686 mailed on Apr. 3, 2012.

Merolli et al., Comparison in in-vivo response between a bioactive glass and a non-bioactive glass, Apr. 2000, pp. 219-222, Journal of Materials Science, vol. 11, No. 4, Kluwer Academic Publishers.

Tilocca et al., The Structure of Bioactive Silicate Glasses: New Insight from Molecular Dynamics Simulations, Jan. 2007, pp. 95-103, Chemistry of Materials, vol. 19, No. 1.

* cited by examiner

NON-AQUEOUS DENTIFRICE COMPOSITION WITH BIOACCEPTABLE AND BIOACTIVE GLASS AND METHODS OF USE AND MANUFACTURE THEREOF

CROSS-REFERENCE TO RELATED APPLICATIONS

The present application is a national stage entry under 35 U.S.C. §371 of International Patent Application No. PCT/US2010/029682, filed Apr. 1, 2010, which claims priority to U.S. Provisional Application No. 61/165,795, filed Apr. 1, 2009, the entries of which are hereby incorporated by reference.

FIELD OF THE INVENTION

The invention encompasses non-aqueous dentifrice compositions containing a bioacceptable and bioactive glass with improved mouth-feel, foam, and product stability. More particularly, the invention encompasses non-aqueous compositions including combinations including carrageenan and/or carboxymethylcellulose gums, glycerin, ethylene oxide/propylene oxide copolymers, and a bioactive glass and methods of use the compositions in an oral care product, for example, a whitening toothpaste, for hypersensitive teeth.

BACKGROUND OF THE INVENTION

Human tooth enamel—consisting primarily of hydroxycarbonate apatite, a crystalline calcium phosphate mineral—naturally undergoes a process of demineralization. Exposure of the enamel to saliva and food leaches minerals from teeth over time and eventually may lead to an increased susceptibility to decay, dentin hypersensitivity, incipient caries, and even carious dentin demineralization.

Bioactive glasses have demonstrated an ability to remineralize teeth and reduce dentin hypersensitivity by reacting with body fluids in the oral cavity to immediately and continuously release calcium and phosphate ions from core silica particles that then crystallize into a stable hydroxycarbonate apatite layer. This crystalline layer is deposited onto and into dentin tubules and effectively both remineralizes teeth and reduces dentin hypersensitivity immediately and in the long term.

A dentifrice composition containing bioactive glass that is suitable for routine daily use to counteract the natural demineralization process is therefore desirable. However, conventional dentifrice compositions including bioactive glass are unsuitable for regular use as for example, toothpastes, because these compositions are water-based and the calcium ions released by the bioactive glass reacts and crosslink with water molecules to form unacceptably thick pastes. The inventors have developed non-aqueous formulations that overcome the difficulty in incorporating conventional gums that provide acceptable mouth-feel and prevent component separation in toothpastes. Accordingly, the invention encompasses non-aqueous dentifrice compositions containing a bioacceptable and bioactive glass that is suitable for routine, regular use and that provides acceptable mouth-feel, foam, and product stability.

SUMMARY OF THE INVENTION

In one embodiment, the invention encompasses non-aqueous dentifrice compositions including: at least one gum selected from the group consisting of carrageenan and carboxymethylcellulose gums; at least one humectant; and a bioacceptable and bioactive glass. Such non-aqueous compositions may then suitably contain other components that are unstable or incompatible with an aqueous environment.

In another embodiment, the invention encompasses non-aqueous dentifrice composition including: from 0.01 wt. % to 5.0 wt. % of at least one gum selected from the group consisting of carrageenan and carboxymethylcellulose gums; from 20.0 wt. % to 80.0 wt. % of at least one humectant; from 1.0 wt. % to 20.0 wt. % of a bioacceptable and bioactive glass; from 1.0 wt. % to 30.0 wt. % of at least one surfactant; from 0.01 wt. % to 10.0 wt. % of a potassium salt; from 0.01 wt. % to 5.0 wt. % of a fluoride salt; and from 0.01 wt. % to 5.0 wt. % of a whitening agent.

In another embodiment, the invention encompasses methods of treating the oral cavity, for example, hypersensitive teeth, including contacting the teeth in a subject in need thereof with a non-aqueous dentifrice composition, wherein the dentifrice composition includes: from 0.01 wt. % to 5.0 wt. % of at least one gum selected from the group consisting of carrageenan and carboxymethylcellulose gums; from 20.0 wt. % to 80.0 wt. % of at least one humectant; from 1.0 wt. % to 20.0 wt. % of a bioacceptable and bioactive glass; from 1.0 wt. % to 30.0 wt. % of at least one surfactant; from 0.01 wt. % to 10.0 wt. % of a potassium salt; from 0.01 wt. % to 5.0 wt. % of a fluoride salt; and from 0.01 wt. % to 5.0 wt. % of a whitening agent.

In another embodiment, the invention encompasses methods of whitening teeth, including for example, hypersensitive teeth, the method including contacting the teeth in a subject in need thereof with a non-aqueous dentifrice composition, wherein the dentifrice composition includes: from 0.01 wt. % to 5.0 wt. % of at least one gum selected from the group consisting of carrageenan and carboxymethylcellulose gums; from 20.0 wt. % to 80.0 wt. % of at least one humectant; from 1.0 wt. % to 20.0 wt. % of a bioacceptable and bioactive glass; from 1.0 wt. % to 30.0 wt. % of at least one surfactant; from 0.01 wt. % to 10.0 wt. % of a potassium salt; from 0.01 wt. % to 5.0 wt. % of a fluoride salt; and from 0.01 wt. % to 5.0 wt. % of a whitening agent.

DETAILED DESCRIPTION OF THE INVENTION

Figure 1:
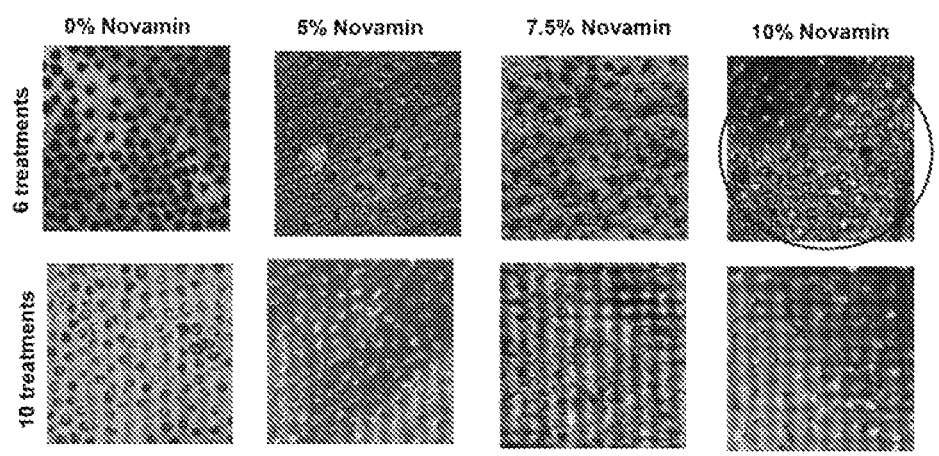
FIG. 1 depicts the results of an in vitro dose response study to determine the optimal bioactive and bio-acceptable glass level for rapid occlusion of tubules.

As used throughout, ranges are used as shorthand for describing each and every value that is within the range. Any value within the range can be selected as the terminus of the range. In addition, all references cited herein are hereby incorporated by reference in their entireties.

As used herein, the term "non-aqueous" means anhydrous or substantially free of water. The individual components of the non-aqueous composition may contain limited amounts of water as long as the overall composition remains substantially free of water.

As used herein, the term "dentifrice" includes any preparation used in cleaning all or a portion of the oral cavity of an individual.

As used herein, the terms "bioacceptable and bioactive glass" and "bioactive glass" mean an inorganic glass material having an oxide of silicon as its major component and that is capable of bonding with growing tissue when reacted with physiological fluids. By way of example, a bioactive glass in accordance with the invention is a glass composition that will form a layer of hydroxycarbonate apatite in vitro when placed in a simulated body fluid. A bioactive glass as used herein is also bioacceptable such that it does not trigger an overwhelmingly adverse immune response in the body, such as in the oral cavity.

As used herein, the term "remineralization" is the formation of hydroxycarbonate apatite on a tooth surface. The formation of hydroxycarbonate apatite begins with exposure of a bioactive glass composition to aqueous solutions. Without being limited by theory, it is believed that the sodium ions ($Na^+$) in the bioactive glass exchanges with $H^+$ ions in body fluids causing pH to increase. Calcium and phosphorus then migrate from the bioactive glass forming a calcium-phosphorous rich surface layer. An underlying silica rich zone slowly increases as the sodium ion in the bioactive glass continues to exchange with the hydrogen ion of the solution. After time, the calcium-phosphorous rich layer crystallizes into a hydroxycarbonate apatite material. Collagen can become structurally integrated with the apatite agglomerates. As hereinafter referred to, an effective remineralizing amount is any amount capable of forming hydroxycarbonate apatite.

As used herein, the term "a tooth structure" refers to any feature or features of a tooth including but not limited to enamel, dentin, pulp, tooth root structure, cementum, root dentin, coronal dentin, and any dental manufacture or combinations thereof. As referred to herein, "tooth" or "teeth" refers to natural teeth, dentures, dental plates, fillings, caps, crowns, bridges, dental implants, and the like, and any other hard surfaced dental prosthesis either permanently or temporarily fixed within the oral cavity.

According to some embodiments, the invention encompasses a non-aqueous dentifrice composition containing a bioacceptable and bioactive glass. In addition, in some embodiments, the present invention describes a method of cleaning and/or whitening hypersensitive teeth including the use of a non-aqueous dentifrice composition containing a bioacceptable and bioactive glass.

General Description

The invention encompasses non-aqueous dentifrice compositions including:
 a. at least one gum selected from the group consisting of carrageenan and carboxymethylcellulose gums;
 b. at least one humectant; and
 c. a bioacceptable and bioactive glass.

In certain embodiments, the at least one gum is a carrageenan gum.

In certain embodiments, the carrageenan gum is selected from the group consisting of: beta-, iota-, kappa-, and lambda-type carrageenans.

In certain embodiments, the at least one carrageenan gum is an iota-carrageenan.

In certain embodiments, the iota-carrageenan is present in an amount of 0.01 wt. % to 5.0 wt. %

In certain embodiments, the at least one gum is a carboxymethylcellulose gum.

In certain embodiments, the carboxymethylcellulose gum is sodium carboxymethylcellulose.

In certain embodiments, the sodium carboxymethylcellulose is present in an amount of from 0.01 wt. % to 5.0 wt. %.

In certain embodiments, the at least one humectant is an anhydrous humectant.

In certain embodiments, the anhydrous humectant is glycerin.

In certain embodiments, the glycerin is present in an amount of from 20.0 wt. % to 80.0 wt. %.

In certain embodiments, the bioacceptable and bioactive glass is calcium sodium phosphosilicate.

In certain embodiments, the calcium sodium phosphosilicate is present in an amount from 1.0 wt. % to 20 wt. %.

In certain embodiments, the compositions further comprise at least one surfactant.

In certain embodiments, the at least one surfactant is sodium lauryl sulfate.

In certain embodiments, the at least one surfactant is a copolymer.

In certain embodiments, the copolymer is an ethylene oxide/propylene oxide copolymer.

In certain embodiments, the compositions further comprise a potassium salt.

In certain embodiments, the potassium salt is potassium chloride.

In certain embodiments, the compositions further comprise a fluoride salt.

In certain embodiments, the fluoride salt is sodium monofluorophosphate.

In certain embodiments, the compositions further comprise a whitening agent.

In certain embodiments, the whitening agent is titanium dioxide.

In certain embodiments, the compositions further comprise a tartar control agent.

In certain embodiments, the compositions further comprise an antibacterial agent.

The invention also encompasses non-aqueous dentifrice compositions, comprising:
 a. from 0.01 wt. % to 5.0 wt. % of at least one gum selected from the group consisting of carrageenan and carboxymethylcellulose gums;
 b. from 20.0 wt. % to 80.0 wt. % of at least one humectant;
 c. from 1.0 wt. % to 20.0 wt. % of a bioacceptable and bioactive glass;
 d. from 1.0 wt. % to 30.0 wt. % of at least one surfactant;
 e. from 0.01 wt. % to 10.0 wt. % of a potassium salt;
 f. from 0.01 wt. % to 5.0 wt. % of a fluoride salt; and
 g. from 0.01 wt. % to 5.0 wt. % of a whitening agent.

In certain embodiments, the at least one gum is a carrageenan gum.

In certain embodiments, the carrageenan gum is selected from the group consisting of: beta-, iota-, kappa-, and lambda-type carrageenans.

In certain embodiments, the at least one carrageenan gum is an iota-carrageenan.

In certain embodiments, the at least one gum is a carboxymethylcellulose gum.

In certain embodiments, the carboxymethylcellulose gum is sodium carboxymethylcellulose.

In certain embodiments, the at least one humectant is an anhydrous humectant.

In certain embodiments, the anhydrous humectant is glycerin.

In certain embodiments, the bioacceptable and bioactive glass is calcium sodium phosphosilicate.

In certain embodiments, the at least one surfactant is sodium lauryl sulfate.

In certain embodiments, the at least one surfactant is a copolymer.

In certain embodiments, the copolymer is an ethylene oxide/propylene oxide copolymer.

In certain embodiments, the potassium salt is potassium chloride.

In certain embodiments, the fluoride salt is sodium monofluorophosphate.

In certain embodiments, the whitening agent is titanium dioxide.

In certain embodiments, the compositions further comprise a tartar control agent.

In certain embodiments, the compositions further comprise an antibacterial agent.

The invention also encompasses methods of cleaning hypersensitive teeth in a subject in need thereof including: contacting said hypersensitive teeth with a non-aqueous dentifrice composition; wherein said dentifrice composition comprises:
 a. from 0.01 wt. % to 5.0 wt. % of at least one gum selected from the group consisting of carrageenan and carboxymethylcellulose gums;
 b. from 20.0 wt. % to 80.0 wt. % of at least one humectant;
 c. from 1.0 wt. % to 20.0 wt. % of a bioacceptable and bioactive glass;
 d. from 1.0 wt. % to 30.0 wt. % of at least one surfactant;
 e. from 0.01 wt. % to 10.0 wt. % of a potassium salt;
 f. from 0.01 wt. % to 5.0 wt. % of a fluoride salt; and
 g. from 0.01 wt. % to 5.0 wt. % of a whitening agent.

The invention also encompasses methods of whitening hypersensitive teeth in a subject in need thereof comprising: contacting said hypersensitive teeth with a non-aqueous dentifrice composition; wherein said dentifrice composition comprises:
 a. from 0.01 wt. % to 5.0 wt. % of at least one gum selected from the group consisting of carrageenan and carboxymethylcellulose gums;
 b. from 20.0 wt. % to 80.0 wt. % of at least one humectant;
 c. from 1.0 wt. % to 20.0 wt. % of a bioacceptable and bioactive glass;
 d. from 1.0 wt. % to 30.0 wt. % of at least one surfactant;
 e. from 0.01 wt. % to 10.0 wt. % of a potassium salt;
 f. from 0.01 wt. % to 5.0 wt. % of a fluoride salt; and
 g. from 0.01 wt. % to 5.0 wt. % of a whitening agent.

Compositions Containing a Bioacceptable and Bioactive Glass

In one embodiment, a non-aqueous dentifrice composition includes: at least one gum selected from the group consisting of carrageenan and carboxymethylcellulose gums or combinations thereof; at least one humectant; and a bioacceptable and bioactive glass.

A. Carrageenan and Carboxymethylcellulose Gums

Gums suitable for use in the invention include, but are not limited to, any carrageenan or carboxymethylcellulose gums or combinations thereof, in any suitable amount or form. In one embodiment, at least one gum is selected from the group consisting of carrageenan and carboxymethylcellulose gums.

In one embodiment, at least one gum is a carrageenan gum. In certain embodiments, the carrageenan gum is selected from the group consisting of: beta-, iota-, kappa-, and lambda-type carrageenan gums. In another embodiment, the carrageenan gum is an iota-carrageenan gum. In another embodiment, at least one gum is a carrageenan present in an amount of from 0.01 wt. % to 5.0 wt. %. In another embodiment, at least one gum is an iota-carrageenan present in an amount of from 0.05 wt. % to 1.0 wt. %. In one embodiment, at least one gum is an iota-carrageenan present in an amount of from 0.1 wt. % to 0.5 wt. %.

In one embodiment, at least one gum is a carboxymethylcellulose gum. In certain embodiments, at least one gum is sodium carboxymethylcellulose. In another embodiment, at least one gum is sodium carboxymethylcellulose in an amount of from 0.01 wt. % to 5.0 wt. %. In one embodiment, at least one gum is sodium carboxymethylcellulose in an amount of from 0.1 wt. % to 3.0 wt. %. In one embodiment, at least one gum is sodium carboxymethylcellulose in an amount of from 0.3 wt. % to 2.0 wt. %.

B. Humectants

Suitable humectants for use in the compositions of the invention include, but are not limited to, any hygroscopic substance capable of incorporation into a non-aqueous dentifrice composition in accordance with the present invention. Suitable humectants include, but are not limited to: glycerin, sorbitol, glyceryl triacetate, xylitol, maltitol, polymeric polyols including polydextrose, quillaia, lactic acid, urea, propylene glycol, and mixtures thereof. In one embodiment, at least one humectant is an anhydrous humectant. In one embodiment, at least one humectant is glycerin. In one embodiment, at least one humectant is present in the compositions in an amount of from 20.0 wt. % to 80.0 wt. %. In certain embodiments, at least one humectant is glycerin in an amount of from 30.0 wt. % to 70.0 wt. %. In one embodiment, at least one humectant is glycerin in an amount of from 40.0 wt. % to 60.0 wt. %.

C. Bioacceptable and Bioactive Glass

Suitable bioacceptable and bioactive glasses for use in the present invention may include, but are not limited to, an inorganic glass material capable of forming a layer of hydroxycarbonate apatite in accordance with the present invention. In one embodiment, the dentifrice composition of the present invention includes a bioactive and bioacceptable glass. In one embodiment, the composition includes calcium sodium phosphosilicate. In one embodiment, the composition includes a bioacceptable and bioactive glass in an amount from 1.0 wt. % to 20 wt. %. In one embodiment, the composition includes a bioacceptable and bioactive glass in an amount from 5.0 wt. % to 15 wt. %. In one embodiment, the composition includes a bioacceptable and bioactive glass in an amount of 10 wt. %.

Suitable bioacceptable and bioactive glasses may have compositions including: from 40 wt. % to 86 wt. % of silicon dioxide ($SiO_2$); from 0 wt. % to 35 wt. % of sodium oxide ($Na_2O$); from 4 wt. % to 46 wt. % of calcium oxide (CaO); and from 1 wt. % to 15 wt. % of phosphorus oxide ($P_2O_5$). Preferably, the bioacceptable and bioactive glass includes: from 40 wt. % to 60 wt. % of silicon dioxide ($SiO_2$); from 10 wt. % to 30 wt. % of sodium oxide ($Na_2O$); from 10 wt. % to 30 wt. % of calcium oxide (CaO); and from 2 wt. % to 8 wt. % of phosphorus oxide ($P_2O_5$). The oxides may be present as solid solutions or mixed oxides, or as mixtures of oxides. Exemplary bioacceptable and bioactive glass suitable for use in the present invention include NovaMin®, which has a composition including 45 wt. % of silicon dioxide, 24.5 wt. % of sodium oxide, 6 wt. % of phosphorus oxide, and 24.5 wt. % of calcium oxide.

In one embodiment, the composition of suitable bioacceptable and bioactive glass may also include: $CaF_2$, $B_2O_3$, $Al_2O_3$, MgO and $K_2O$, in addition to silicon, sodium, phosphorus and calcium oxides. The preferred range for $CaF_2$ is from 0 wt. % to 25 wt. %. The preferred range for $B_2O_3$ is from 0 wt. % to 10 wt. %. The preferred range for $Al_2O_3$ is from 0 wt. % to 4 wt. %. The preferred range for MgO is from 0 wt. % to 5 wt. %. The preferred range for $K_2O$ is from 0 wt. % to 8 wt. %.

In one embodiment, bioacceptable and bioactive glass suitable for use in the present invention is particulate, non-interlinked bioactive glass. In one embodiment, the glass has a particle size range of less than 90 µm. In one embodiment, the glass has a particle size range of less than 70 µm. In one embodiment, the glass has a particle size range of less than 50 µm. In one embodiment, the glass has a particle size range of less than 40 µm. In one embodiment, the glass has a particle size range of less than 30 µm. In one embodiment, the glass has a particle size range of less than 20 µm. In certain embodiments, the particle size of the bioactive glass portion of the compositions is less than 20, 10, 5, 4, 3, 2, 1 micron.

In an embodiment, a glass has a median particle size between 0.5 µm and 90 µm. In another embodiment, a glass has median a particle size between 0.5 µm and 70 µm. In another embodiment, a glass has a median particle size between 0.5 µm and 50 µm. In another embodiment, a glass has a median particle size between 0.5 µm and 40 µm. In another embodiment, a glass has a median particle size between 0.5 µm and 30 µm. In another embodiment, a glass has a median particle size between 0.5 µm and 20 µm. In another embodiment, a glass has a median particle size between 0.5 µm and 10 µm. In another embodiment, a glass has a median particle size between 0.5 µm and 5 µm. In another embodiment, a glass has a median particle size between 0.5 µm and 4 µm. In another embodiment, a glass has a median particle size between 0.5 µm and 3 µm. In another embodiment, a glass has a median particle size between 0.5 µm and 2 µm. In another embodiment, a glass has a median particle size between 0.5 µm and 1 µm. In yet another embodiment, a glass has a median particle size selected from the group consisting of 0.5 µm, 1 µm, 2 µm, 3 µm, 4 µm, 5 µm, 7.5 µm and 10 µm.

In certain embodiments, the larger of these particles (e.g., less than 90 microns to less than 20 microns) provide a reservoir of additional calcium and phosphorous so that the mineralization, or depositing of the calcium phosphate layer begun by the small particles (e.g., less than 20 microns to less than 1 micron) can continue. In certain embodiments of the invention, additional calcium and phosphorous can be leached to all tooth structure as well as to particles, which have become attached to the inside or at the openings of surface irregularities of tooth structure such as dentinal tubules. This in turn provides for continuation of the entire reaction and continued growth of the smaller of these particles, which have lodged inside or over the openings of such surface irregularities and can result in effectively coating or filling the surface irregularity. This excess concentration of ions of calcium and phosphorous allows reaction of the smaller of these particles to take place because the smaller particles quickly exhaust their ions because of their relatively high surface area. The larger of these particles will react and release their ions more slowly as a longer term effect. Furthermore, the larger of these particles will mechanically abrade the tooth surface opening various surface irregularities allowing small particles to enter and react with the surface irregularity.

This effect is very beneficial in a variety of applications. For example, in preventing caries or decay, the compositions of the invention are capable of penetrating into the depths of the smallest of surface irregularities and receiving a continued supply of ions from larger nearby particles so that it is able to grow after exhausting its stored ion supply. This is also very useful in sealing pits and fissures, and a much more effective and long lasting seal is obtained.

The occlusion of these tubules leads to a significant reduction in the amount of sensitivity after, for example, periodontal surgery. In certain embodiments, a mixture of particles less than two microns and larger than 45 microns in diameter are used. It has been found that this combination yields a particularly effective composition.

In certain embodiments, the bio-acceptable and bioactive glass encompasses glass compositions including the following components by weight:

| Ingred. | wt. % |
|---|---|
| $SiO_2$ | 40-60 |
| $CaO_2$ | 10-30 |
| $Na_2O$ | 10-35 |
| $P_2O_5$ | 2-8 |
| $CaF_2$ | 0-25 |
| $B_2O_3$ | 0-10 |

In certain embodiments, the following composition by weight percentage encompasses a bioactive glass:

| Ingred. | wt. % |
|---|---|
| $SiO_2$ | 40-60 |
| $CaO_2$ | 10-30 |
| $Na_2O$ | 10-35 |
| $P_2O_5$ | 2-8 |
| $CaF_2$ | 0-25 |
| $B_2O_3$ | 0-10 |
| $K_2O$ | 0-8 |
| MgO | 0-5 |

D. Other Additives

In certain embodiments, the non-aqueous dentifrice composition of the invention may include any another additive conventionally used in dentifrice formulations. Any suitable additive in any suitable amount or form may be used. Suitable additives for use in the invention include, but are not limited to: surfactants, desensitizing agents including potassium salts, fluorine sources, whitening agents, tartar control agents, antibacterial agents, abrasives including silica, binders and thickening agents, detergents, adhesion agents, foam modulators, pH modifying agents, mouth-feel agents, sweeteners, flavorants, colorants, preservatives, Gantrez, amelogenin, milk proteins (casein), chitosan, pluracare L1220 (ethylene oxide/propylene oxide copolymer), polyox, PVP, methacrylates, shellac, arginine, and combinations thereof, and the like. It is to be understood that these additives are optional components and can be, individually or collectively, excluded from the automatic dishwashing composition of the present invention. It is further understood that while general attributes of each of the above categories of materials may differ, there may be some common attributes and any given material may serve multiple purposes within two or more of such categories of materials. In certain embodiments, such additives are selected for compatibility with the bioactive glass and with other ingredients of the composition.

1. Surfactants

Surfactants suitable for use in the invention include but are not limited to: anionic surfactants, nonionic surfactants, cationic surfactants, amphoteric surfactants, ampholytic surfactants, zwitterionic surfactants, and mixtures thereof, as known to one of ordinary skill in the art. Suitable surfactants may be added in any suitable amount or form, may optionally be in a surfactant system, and may be added to provide any desired properties including, but not limited to, cleaning and/or foaming properties. Suitable surfactants may include anionic, cationic, nonionic and amphoteric surfactants.

In one embodiment, a dentifrice composition of the present invention includes at least one surfactant. In one embodiment, a composition including at least one surfactant includes sodium lauryl sulfate. In one embodiment, a composition includes sodium lauryl sulfate in an amount from 0.5 wt. % to 10 wt. %. In one embodiment, a composition includes sodium lauryl sulfate in an amount from 1 wt. % to 5 wt. %. In one embodiment, a composition includes sodium lauryl sulfate in an amount from 1.5 wt. % to 2 wt. %.

In one embodiment, a dentifrice composition of the invention including at least one surfactant includes a copolymer. In one embodiment, a composition including a copolymer includes an ethylene oxide/propylene oxide copolymer. In one embodiment, a composition including a copolymer includes an ethylene oxide/propylene oxide copolymer in an amount from 1.0 wt. % to 45.0 wt. %. In one embodiment, a composition including a copolymer includes an ethylene oxide/propylene oxide copolymer in an amount from 5.0 wt. % to 35.0 wt. %. In one embodiment, a composition including a copolymer includes an ethylene oxide/propylene oxide copolymer in an amount from 10.0 wt. % to 25.0 wt. %.

2. Desensitizing Agents

Desensitizing agents suitable for use in the present invention may include any therapeutically effective agent suitable for use in an oral cavity. Suitable desensitizing agents may include, but are not limited to, strontium and potassium salts. In one embodiment, a dentifrice composition of the present invention includes a desensitizing agent. In one embodiment, a dentifrice composition of the present invention includes a potassium salt. In one embodiment, the potassium salt is selected from the group consisting of, but not limited to: potassium bicarbonate, potassium citrate, potassium chloride, or potassium nitrate. In one embodiment, a dentifrice composition of the present invention includes potassium chloride. In one embodiment, a dentifrice composition of the present invention includes potassium chloride in an amount of 0.1 wt. % to 10 wt. %. In one embodiment, a dentifrice composition of the present invention includes potassium chloride in an amount of 1 wt. % to 5 wt. %. In one embodiment, a dentifrice composition of the present invention includes potassium chloride in an amount of 2 wt. % to 4 wt. %.

3. Fluoride Sources

Fluoride sources suitable for use in the present invention may include any orally acceptable particulated fluoride-ion containing agent formulated to not interfere with the efficacy of the bioactive glass, and that may be useful, for example, as an anti-caries agent. Suitable fluorine sources may include, but are not limited to: ionic fluorides including alkali metal fluorides; amine fluorides such as olaflur (N'-octadecyltrimethylendiamine-N,N,N'-tris(2-ethanol)-dihydrofluoride); stannous fluoride; indium fluoride; and ionic monofluorophosphates including alkali metal monofluorophosphates such as potassium, sodium and ammonium fluorides and monofluorophosphates; and mixtures thereof.

In one embodiment, a dentifrice composition of the present invention further includes a fluoride source. In one embodiment, a composition further includes a fluoride salt. In one embodiment, a composition further including a fluoride salt includes sodium monofluorophosphate. In one embodiment, calcium glycerophosphate, which has been shown to enhance the activity of ionic monofluorophosphates, may be optionally added when the fluoride source is an ionic monofluorophosphate. In one embodiment, a composition may include a fluorine source providing 100 and 3000 ppm of fluoride. In one embodiment, a composition may include a fluorine source providing 500 and 2000 ppm of fluoride.

4. Whitening Agents

Whitening agents suitable for use in the present invention may include any therapeutically effective agent suitable for use in an oral cavity. Suitable whitening agents include, but are not limited to: titanium dioxide, hydrogen peroxide, sodium tripolyphosphate, and the like. In one embodiment, a dentifrice composition of the present invention further includes a whitening agent. In one embodiment, a composition of the present invention further includes titanium dioxide. In one embodiment, titanium dioxide may be included at appropriate levels.

5. Abrasives

Abrasives suitable for use in the present invention may include any orally acceptable particulated agent formulated to not interfere with the efficacy of the bioactive glass. Suitable abrasives for use in the present invention may include, but are not limited to: silica, zinc orthophosphate, sodium bicarbonate (baking soda), plastic particles, alumina, hydrated alumina, calcium carbonate, calcium pyrophosphate, and mixtures thereof. The silica abrasive may be a natural amorphous silica including diatomaceous earth; or a synthetic amorphous silica such as a precipitated silica; or a silica gel, such as a silica xerogel; or mixtures thereof.

Generally, an amount of abrasive suitable for use in the dentifrice composition of the invention will be empirically determined to provide an acceptable level of cleaning and polishing, in accordance with the techniques well known in the art. In one embodiment, a dentifrice composition of the present invention includes an abrasive. In one embodiment, a composition includes a silica abrasive. In one embodiment, a silica abrasive is present in an amount of from 1 wt. % to 30 wt. %. In one embodiment, a silica abrasive is present in an amount of from 5 wt. % to 15 wt. %. In one embodiment, a silica abrasive is present in an amount of from 7 wt. % to 10 wt. %.

6. Mouth-feel Agents

Mouth-feel agents suitable for use in the present invention may include any orally acceptable materials imparting a desirable texture or other feeling during use of the dentifrice composition, in any form or amount. Suitable mouth-feel agents may include, but are not limited to: dispersed flavorants, sweeteners, saliva-stimulating agents, and the like.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, alpha-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of 0.01% to 5%, optionally in various embodiments from 0.05 to 2%, from 0.1% to 2.5%, and from 0.1 to 0.5%.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from 0.005% to 5%, optionally from 0.01% to 1%.

The compositions of the present invention may optionally comprise a saliva stimulating agent formulated to not interfere with the efficacy of the bioactive glass and/or potassium salts described in detail herein and useful, for example, in amelioration of dry mouth. One or more saliva stimulating agents are optionally present in saliva stimulating effective total amount.

7. Other Actives

In some embodiments, compositions of the invention may optionally include other active materials, operable for the prevention or treatment of a condition or disorder of hard or soft tissue of the oral cavity, or the prevention or treatment of a physiological disorder or condition. In some embodiments, the active is a "systemic active" which is operable to treat or prevent a disorder that, in whole or in part, is not a disorder of the oral cavity. In some embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, antiplaque agents, periodontal actives, abrasives, breath freshening agents, tooth desensitizers, salivary stimulants, and combinations thereof.

In some embodiments, compositions of the invention may optionally comprise a tartar control (anti-calculus) agent formulated to not interfere with the efficacy of the bioactive glass and/or potassium salts described in detail herein. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclo-pentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

In some embodiments, compositions of the invention may optionally include an antibacterial agent formulated to not interfere with the efficacy of the bioactive glass and/or potassium salts described in detail herein. Examples of antibacterial agents include, but are not limited to, triclosan, cetylpyridinium chloride, and combinations thereof.

In some embodiments, compositions of the present invention include comprise a nutrient formulated to not interfere with the efficacy of the bioactive glass and/or potassium salts described in detail herein. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In some embodiments, compositions of the present invention may also contain an antistain agent. Suitable antistain agents may include, but are not limited to: carboxylic acids, amino carboxylate compounds, phosphonoacetic acid, polyvinylpyrrolidone, and the like. The antistain agent may be incorporated into the dentifrice composition or may be provided as a separate composition, for use after the dentifrice.

II. Methods of Treating and Preventing Disorders of the Oral Cavity

The dentifrice compositions of the invention include, in part, a bioacceptable and bioactive glass that is useful in treating or preventing in a subject in need thereof various disorders of the oral cavity, for example, enamel remineralization, incipient caries remineralization, carious dentin remineralization, caries prevention, arresting decay, reversing decay, anti-caries, pit and fissure sealants, prophylactic pastes, fluoride treatments, dentinal sealants, and combinations thereof. As used herein, the term "subject" includes mammals, for example, humans and companion animals including cats and dogs.

In one embodiment, a method of cleaning hypersensitive teeth in a subject in need thereof includes contacting the teeth or a tooth surface with a non-aqueous dentifrice composition of the invention, which includes one or more bioactive and bioacceptable glasses, one or more humectants, and at least one gum selected from the group consisting of carrageenan and carboxymethylcellulose gums. In certain embodiments, the dentifrice composition includes: from 0.01 wt. % to 5.0 wt. % of at least one gum selected from the group consisting of carrageenan and carboxymethylcellulose gums; from 20.0 wt. % to 80.0 wt. % of at least one humectant; from 1.0 wt. % to 20.0 wt. % of a bioacceptable and bioactive glass; from 1.0 wt. % to 30.0 wt. % of at least one surfactant; from 0.01 wt. % to 10.0 wt. % of a potassium salt; from 0.01 wt. % to 5.0 wt. % of a fluoride salt; and from 0.01 wt. % to 5.0 wt. % of a whitening agent.

In another embodiment, a method of whitening hypersensitive teeth in a subject in need thereof includes contacting the teeth or a tooth surface with a non-aqueous dentifrice composition of the invention, which includes one or more bioactive and bioacceptable glasses, one or more humectants, and at least one gum selected from the group consisting of carrageenan and carboxymethylcellulose gums. In certain embodiments, the dentifrice composition includes: the use of a non-aqueous dentifrice composition, wherein the dentifrice composition includes: from 0.01 wt. % to 5.0 wt. % of at least one gum selected from the group consisting of carrageenan and carboxymethylcellulose gums; from 20.0 wt. % to 80.0 wt. % of at least one humectant; from 1.0 wt. % to 20.0 wt. % of a bioacceptable and bioactive glass; from 1.0 wt. % to 30.0 wt. % of at least one surfactant; from 0.01 wt. % to 10.0 wt. % of a potassium salt; from 0.01 wt. % to 5.0 wt. % of a fluoride salt; and from 0.01 wt. % to 5.0 wt. % of a whitening agent.

In another embodiment, the invention encompasses a method of treating dental hypersensitivity in a subject in need thereof including contacting the teeth or a tooth surface with a non-aqueous dentifrice composition of the invention, which includes one or more bioactive and bioacceptable glasses, one or more humectants, and at least one gum selected from the group consisting of carrageenan and carboxymethylcellulose gums.

Additional methods of treating or preventing disorders of the oral cavity in a subject in need thereof are also included within the scope of the invention. In one embodiment, a method of at least partially occluding dentin tubules in a subject in need thereof includes contacting the teeth or a tooth surface with a non-aqueous dentifrice composition in accordance with the present invention. In one embodiment, a method of preventing tooth decay in a subject in need thereof includes contacting the teeth or a tooth surface with a non-aqueous dentifrice composition in accordance with the present invention. In one embodiment, a method of treating tooth decay in a subject in need thereof includes contacting the teeth or a tooth surface with a non-aqueous dentifrice composition in accordance with the present invention. In one embodiment, a method of preventing incipient carries in a subject in need thereof includes contacting the teeth or a tooth surface with a non-aqueous dentifrice composition in accordance with the present invention. In one embodiment, a method of remineralizing enamel in a subject in need thereof includes contacting the teeth or a tooth surface with a non-aqueous dentifrice composition in accordance with the present invention. In one embodiment, a method of sealing fissures in a subject in need thereof includes contacting the teeth or a tooth surface with a non-aqueous dentifrice composition in accordance with the present invention. In one embodiment, a method of sealing pits in a subject in need thereof includes contacting the teeth or a tooth surface with a non-aqueous dentifrice composition in accordance with the present invention. In one embodiment, a method of lining tooth structure in a subject in need thereof includes contacting the teeth or a tooth surface with a non-aqueous dentifrice composition in accordance with the present invention. In one embodiment, a method for capping pulp in a subject in need thereof includes contacting the teeth or a tooth surface with a non-aqueous dentifrice composition in accordance with the present invention. In one embodiment, a method for treating tooth structure after periodontal surgery in a subject in need thereof includes contacting the teeth or a tooth surface with a non-aqueous dentifrice composition in accordance with the present invention.

EXAMPLES

Example 1

The following examples further describe and demonstrate some embodiments within the scope of the present invention. These examples are given solely for the purpose of illustration and are not to be construed as limitations of the present invention as many variations thereof are possible without departing from the scope and spirit of the present invention.

A. Method of Processing a Non-Aqueous Dentifrice Composition with Bioacceptable and Bioactive Glass The following procedure was followed for each exemplary dentifrice composition containing bioacceptable and bioactive glass.

1. A formula amount of glycerin was loaded to a suitable beaker. Saccharin, titanium dioxide, and gum were slowly added and mixed until well-dispersed. The beaker and contents were heated to 150° F. and mixed for fifteen (15) minutes.

2. Pluracare® L1220 PEG/PPG co-polymer was added to the ross mixer pot. The contents of the beaker in Step 1 were transferred to the ross pot and mixed for five (5) minutes with vacuum. After that time, the ross cover was opened and the temperature was checked. If the temperature was over 120° F., Step 2 was repeated. When the temperature cools to 120° F. or below, the sodium monofluorophosphate (MFP), bioactive glass (NovaMin®), silica thickener (Zeodent® 165) and silica abrasive (Zeodent® 114) were added, then mixed until the powders were wet. The vacuum was pulled, and the contents in the ross pot mixed for twenty (20) minutes on high speed.

3. The temperature was checked. The temperature should be 110° F. or below. Flavor and sodium lauryl sulfate powder was added, and then the composition mixed on ten (10) minutes on high speed under full vacuum.

TABLE 1

Exemplary Compositions Containing Bioactive Glass

| Ingredient | Composition A | Composition B | Composition C | Composition D | Composition E |
|---|---|---|---|---|---|
| Glycerin | 63.2 | 46 | 63.4 | 63.5 | 52.5 |
| Pluracare® L1220 | 5 | 22 | 5 | 5 | 5 |
| Sodium CMC | | 1 | 0.3 | | 1.75 |
| Carrageenan PS223 | 0.5 | | 0.3 | | |
| Carrageenan PS298 | | | | 0.5 | |
| Sodium MFP | 1.1 | 1.1 | 1.1 | 1.1 | 1.1 |
| Potassium Chloride | | | | | 3.75 |
| Saccharin | 0.3 | 0.3 | 0.3 | 0.3 | 0.3 |
| Titanium Dioxide | 1 | 1 | 1 | 1 | 1 |
| Bioactive Glass (NovaMin®) | 10 | 10 | 10 | 10 | 10 |
| Silica thickener (Zeodent® 165) | 8 | 8 | 8 | 8 | 20 |
| Silica abrasive (Zeodent® 114) | 8 | 8 | 8 | 8 | 2 |
| Flavor | 1.2 | 0.9 | 0.9 | 0.9 | 0.9 |
| SLS | 1.7 | 1.7 | 1.7 | 1.7 | 1.7 |
| TOTAL: | 100 | 100 | 100 | 100 | 100 |

TABLE 2

MFP-containing Samples.

| | 1450 ppm MFP | 1450 ppm MFP 8% Arginine/5% PCP | 1450 ppm MFP KCL |
|---|---|---|---|
| Glycerin | 63.000 | 48.800 | 58.850 |
| KCl | 0.000 | 0.000 | 3.750 |
| Pluracare L1220 | 5.000 | 5.000 | 5.000 |
| Iota Carrageenan | 0.300 | 0.400 | 0.000 |
| CMC 7MF | 0.300 | 0.400 | 0.000 |
| CMC 2000S | 0.000 | 0.000 | 1.000 |
| MFP | 1.100 | 1.100 | 1.100 |
| NaF | 0.000 | 0.000 | 0.000 |
| SnF2 | 0.000 | 0.000 | 0.000 |
| saccharin | 0.300 | 0.300 | 0.300 |
| Sucralose | 0.000 | 0.000 | 0.000 |
| Zn•Citrate | 0.000 | 0.000 | 0.000 |
| L-Arginine | 0.000 | 8.000 | 0.000 |
| TiO2 | 1.000 | 1.000 | 1.000 |
| Bioactive Glass | 10.000 | 10.000 | 10.000 |

TABLE 2-continued

MFP-containing Samples.

|  | 1450 ppm MFP | 1450 ppm MFP 8% Arginine/5% PCP | 1450 ppm MFP KCL |
|---|---|---|---|
| Thickening Silica | 8.000 | 9.000 | 8.000 |
| Precipitate Calcium Carbonate | 0.000 | 5.000 | 0.000 |
| Abrasive silica | 8.000 | 8.000 | 8.000 |
| flavor | 1.300 | 1.300 | 1.300 |
| SLS | 1.700 | 1.700 | 1.700 |
| Total: | 100.000 | 100.000 | 100.000 |

TABLE 3

NaF-containing Samples.

|  | 1450 ppm NaF | 1100 ppm NaF |
|---|---|---|
| Glycerin | 63.880 | 64.057 |
| KCl | 0.000 | 0.000 |
| Pluracare L1220 | 5.000 | 5.000 |
| Iota Carrageenan | 0.300 | 0.300 |
| CMC 7MF | 0.300 | 0.300 |
| CMC 2000S | 0.000 | 0.000 |
| MFP | 0.000 | 0.000 |
| NaF | 0.320 | 0.243 |
| SnF2 | 0.000 | 0.000 |
| saccharin | 0.300 | 0.300 |
| Sucralose | 0.000 | 0.000 |
| Zn•Citrate | 0.000 | 0.000 |
| L-Arginine | 0.000 | 0.000 |
| TiO2 | 1.000 | 1.000 |
| Bioactive Glass | 10.000 | 10.000 |
| Thickening Silica | 8.000 | 8.000 |
| Precipitate Calcium Carbonate | 0.000 | 0.000 |
| Abrasive silica | 8.000 | 8.000 |
| flavor | 1.200 | 1.100 |
| SLS | 1.700 | 1.700 |
| Total: | 100.000 | 100.000 |

TABLE 4

SnF-containing Samples.

|  | 1100 ppm SnF$_2$ | 1100 ppm SnF$_2$/ZnCl |
|---|---|---|
| Glycerin | 62.726 | 61.726 |
| KCl | 0.000 | 0.000 |
| Pluracare L1220 | 5.000 | 5.000 |
| Iota Carrageenan | 0.400 | 0.400 |
| CMC 7MF | 0.400 | 0.400 |
| CMC 2000S | 0.000 | 0.000 |
| MFP | 0.000 | 0.000 |
| NaF | 0.000 | 0.000 |
| SnF2 | 0.454 | 0.454 |
| saccharin | 0.000 | 0.000 |
| Sucralose | 0.120 | 0.120 |
| Zn•Citrate | 0.000 | 2.000 |
| L-Arginine | 0.000 | 0.000 |
| TiO2 | 1.000 | 1.000 |
| Bioactive Glass | 10.000 | 10.000 |
| Thickening Silica | 9.000 | 8.000 |
| Precipitate Calcium Carbonate | 0.000 | 0.000 |
| Abrasive silica | 8.000 | 8.000 |
| flavor | 1.200 | 1.200 |
| SLS | 1.700 | 1.700 |
| Total: | 100.000 | 100.000 |

Example 2

Single-tube Toothpaste Product Including Occlusion Agent(s) and Potassium Salt(s) that Offers Superior Tooth Sensitivity Relief An illustrative embodiment of the invention encompasses a single tube toothpaste product including one or more inclusion agents and one or more potassium salts. In one illustrative embodiment, to deliver faster relief, a single tube technology that combines rapid occlusion agents, for example, a bioactive and bio-acceptable glass (e.g., Novamin) with potassium is made. The non-aqueous bioactive and bio-acceptable glass formulations with potassium were found to provide significant in vitro occlusion.

In another illustrative embodiment, the bioactive and bio-acceptable glass (e.g., Novamin) formula is surprising found to possess additional occlusion benefit by adding commercially available small particle silica (e.g., Sorbosil AC-43).

An in vitro dose response study was performed to determine the optimal bioactive and bio-acceptable glass (e.g., Novamin) level for rapid occlusion (FIG. 1). Products with the bioactive and bio-acceptable glass (e.g., Novamin) at 5%, 7.5% and 10% were prepared. Products were evaluated by confocal microscopy after 6 and 10 brushings. After six treatments, the 10% bioactive and bio-acceptable glass (e.g., Novamin) formula showed significant occlusion while all bioactive and bio-acceptable glass (e.g., Novamin) levels provided significant occlusion after 10 treatments.

To boost the 5% bioactive and bio-acceptable glass (e.g., Novamin) occlusion at six treatments, the effect of addition of silica (e.g., Ineos AC43 silica) was studied in vitro. As shown in the confocal microscopy images below, the addition of 9% silica (e.g., Ineos AC43 silica) significantly improved occlusion at six treatments.

Figure 2:
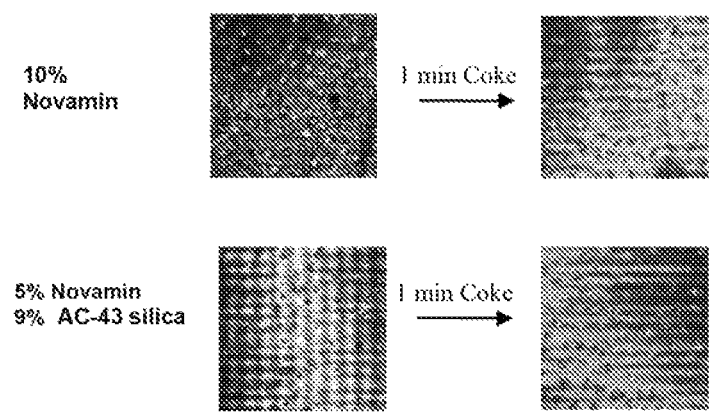
FIG. 2 depicts the acid resistance of the two systems set forth herein, as tested in vitro.

The acid resistance of the two leading systems was evaluated in vitro (FIG. 2). The 6-treatment dentin disks were soaked for 1 minute in Coke Classic. Images are shown below. Both systems showed significant resistance to acid challenge.

To add body and prevent separation, various gums were added to the non-aqueous glycerin based formulas. In certain embodiments, carboxymethylcellulose provided the best overall mouthfeel. Carbopol provided body, but in certain embodiments imparted a sticky feel. The formulas were optimized. All lead formulas were stabile at 4 weeks at 40° C.

10% Novamin/20% Pluraflo/CMC (no KCl)

10% Novamin/3.75% KCL/CMC

5% Novamin/3.75% KCL/9% AC43/CMC

Example 3

Figure 3:
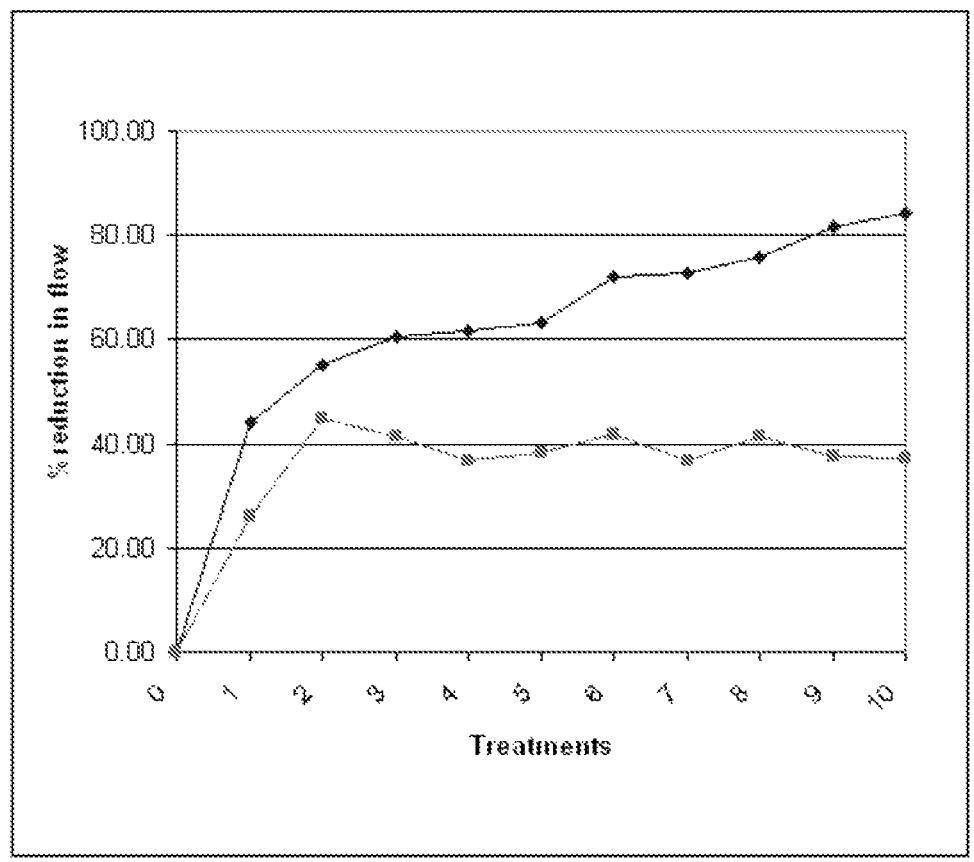
FIG. 3 depicts the results of conductance experiments with 10% Novamin toothpaste vs. conventional non-occlusion silica toothpaste control. Confocal laser microscopy images illustrate Novamin dose response and the boosting effect of AC43 silica. The top line represents Novamin, the bottom line represents the control sample.

Illustrated in FIG. 3 is a graph depicting conductance data with 10% Novamin toothpaste vs. conventional non-occlusion silica toothpaste control and confocal laser microscopy images showing Novamin dose response and boosting effect of AC43 silica. The top line is the Novamin sample and the bottom line is the control sample.

TABLE 5

Conductance measurements.

| | Average Conductance | | | |
|---|---|---|---|---|
| Treatments | % reduction Novamin 10% | stdev | % reduction Control | stdev |
| 0 | 0.00 | 0.00 | 0.00 | 0 |
| 1 | 44.03 | 28.08 | 26.05 | 16.87 |
| 2 | 55.17 | 17.74 | 44.64 | 38.75 |
| 3 | 60.63 | 15.21 | 41.19 | 34.54 |
| 4 | 61.67 | 14.19 | 36.92 | 20.45 |
| 5 | 63.33 | 13.41 | 38.35 | 16.8 |
| 6 | 71.94 | 8.19 | 41.73 | 16.54 |
| 7 | 72.95 | 9.19 | 36.63 | 16.77 |
| 8 | 76.02 | 11.07 | 41.40 | 14.13 |
| 9 | 81.57 | 11.90 | 37.63 | 12.44 |
| 10 | 84.30 | 11.21 | 37.17 | 15.99 |

The invention is not to be limited in scope by the specific embodiments disclosed in the examples, which are intended as illustrations of a few aspects of the invention, and any embodiments, which are functionally equivalent, are within the scope of this invention. Indeed, various modifications of the invention in addition to those shown and described herein will become apparent to those skilled in the art and are intended to fall within the appended claims.

For any references that have been cited, the entire disclosures of which are incorporated herein by reference.

What is claimed is:

1. A non-aqueous dentifrice composition, comprising:
   a. from 0.01 wt. % to 5.0 wt. % of at least one gum selected from the group consisting of carrageenan and carboxymethylcellulose gums;
   b. from 20.0 wt. % to 80.0 wt. % of at least one humectant;
   c. from 1.0 wt. % to 20.0 wt. % of a bioacceptable and bioactive glass;
   d. from 1.0 wt. % to 30.0 wt. % of at least one surfactant;
   e. from 0.01 wt. % to 10.0 wt. % of a potassium salt;
   f. from 0.01 wt. % to 5.0 wt. % of a fluoride salt; and
   g. from 0.01 wt. % to 5.0 wt. % of a whitening agent,
   wherein the oral care composition provides a fluid flow rate of no greater than about 45% of the fluid flow rate of etched dentin.

2. The dentifrice composition of claim 1, wherein said at least one gum is a carrageenan gum.

3. The dentifrice composition of claim 2, wherein said carrageenan gum is selected from the group consisting of: beta-, iota-, kappa-, and lambda-type carrageenans.

4. The dentifrice composition of claim 3, wherein said at least one carrageenan gum is an iota-carrageenan.

5. The dentifrice composition of claim 1, wherein said at least one gum is a carboxymethylcellulose gum.

6. The dentifrice composition of claim 5, wherein said carboxymethylcellulose gum is sodium carboxymethylcellulose.

7. The dentifrice composition of claim 1, wherein said at least one humectant is an anhydrous humectant.

8. The dentifrice composition of claim 7, wherein said anhydrous humectant is glycerin.

9. The dentifrice composition of claim 1, wherein said bioacceptable and bioactive glass is calcium sodium phosphosilicate.

10. The dentifrice composition of claim 1, wherein said at least one surfactant is sodium lauryl sulfate.

11. The dentifrice composition of claim 1, wherein said at least one surfactant is a copolymer.

12. The dentifrice composition of claim 11, wherein said copolymer is an ethylene oxide/propylene oxide copolymer.

13. The dentifrice composition of claim 1, wherein said potassium salt is potassium chloride.

14. The dentifrice composition of claim 1, wherein said fluoride salt is sodium monofluorophosphate.

15. The dentifrice composition of claim 1, wherein said whitening agent is titanium dioxide.

16. The dentifrice composition of claim 1, further comprising a tartar control agent.

17. The dentifrice composition of claim 1, further comprising an antibacterial agent.

18. A method of cleaning or whitening hypersensitive teeth comprising: contacting said hypersensitive teeth in a subject in need thereof with the non-aqueous dentifrice composition of claim 1,
   wherein the oral care composition provides a fluid flow rate of no greater than about 45% of the fluid flow rate of etched dentin.

19. The dentifrice composition of claim 7, wherein said anhydrous humectant is glycerin and said bioacceptable and bioactive glass is calcium sodium phosphosilicate.

20. The dentifrice composition of claim 19, wherein said at least one surfactant is sodium lauryl sulfate and said potassium salt is potassium chloride.

21. The dentifrice composition of claim 20, wherein said fluoride salt is sodium monofluorophosphate and said whitening agent is titanium dioxide.

22. The dentifrice composition of claim 7, further comprising a tartar control agent.

23. The dentifrice composition of claim 7, further comprising an antibacterial agent.

24. The dentifrice composition of claim 21, further comprising a tartar control agent.

25. The dentifrice composition of claim 21, further comprising an antibacterial agent.

* * * * *